(12) United States Patent
Handa

(10) Patent No.: US 10,325,692 B2
(45) Date of Patent: Jun. 18, 2019

(54) X-RAY DIFFRACTIVE GRATING AND X-RAY TALBOT INTERFEROMETER

(71) Applicant: CANON KABUSHIKI KAISHA, Tokyo (JP)

(72) Inventor: Soichiro Handa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 176 days.

(21) Appl. No.: 15/332,420

(22) Filed: Oct. 24, 2016

(65) Prior Publication Data

US 2017/0125134 A1 May 4, 2017

(30) Foreign Application Priority Data

Oct. 30, 2015 (JP) ................................. 2015-215212

(51) Int. Cl.
| | | |
|---|---|---|
| *G21K 1/06* | (2006.01) | |
| *G01N 23/20* | (2018.01) | |
| *G01N 23/04* | (2018.01) | |

(52) U.S. Cl.
CPC ............... *G21K 1/06* (2013.01); *G01N 23/04* (2013.01); *G01N 23/20075* (2013.01); *G21K 2201/067* (2013.01); *G21K 2207/005* (2013.01)

(58) Field of Classification Search
None
See application file for complete search history.

(56) References Cited

U.S. PATENT DOCUMENTS

| | | | | |
|---|---|---|---|---|
| 5,812,629 | A * | 9/1998 | Clauser .................. | A61B 6/032 378/37 |
| 2003/0092075 | A1* | 5/2003 | Pepper .................. | B01L 3/5085 435/7.9 |
| 2010/0260315 | A1* | 10/2010 | Sato ......................... | G21K 1/06 378/36 |
| 2010/0290590 | A1* | 11/2010 | Ouchi ..................... | G01N 23/04 378/62 |
| 2011/0182403 | A1* | 7/2011 | Nakamura ............... | G21K 1/06 378/36 |
| 2013/0034209 | A1* | 2/2013 | Ouchi ..................... | A61B 6/484 378/62 |
| 2013/0208864 | A1* | 8/2013 | Rossl ...................... | A61B 6/484 378/62 |
| 2016/0256122 | A1* | 9/2016 | Heid ...................... | A61B 6/4035 |

OTHER PUBLICATIONS

Atsushi Momose, et al., "X-ray Talbot Interferometry with Capillary Plates", Japanese Journal of Applied Physics, Jan. 10, 2006, pp. 314-316, vol. 45, No. 1A, The Japan Society of Applied Physics.

* cited by examiner

*Primary Examiner* — Hoon K Song
(74) *Attorney, Agent, or Firm* — Canon U.S.A., Inc. IP Division

(57) ABSTRACT

An X-ray diffractive grating includes a phase advance portion and a plurality of phase delay portions. The phase advance portion includes a grating material. In each of the phase delay portions, the thickness of the grating material is less than that in the phase advance portion, and the area occupancy of the phase delay portions in the corresponding two-dimensional grating pattern is 15% or more but less than 45%. The phase delay portions are arranged in a hexagonal lattice shape.

9 Claims, 6 Drawing Sheets

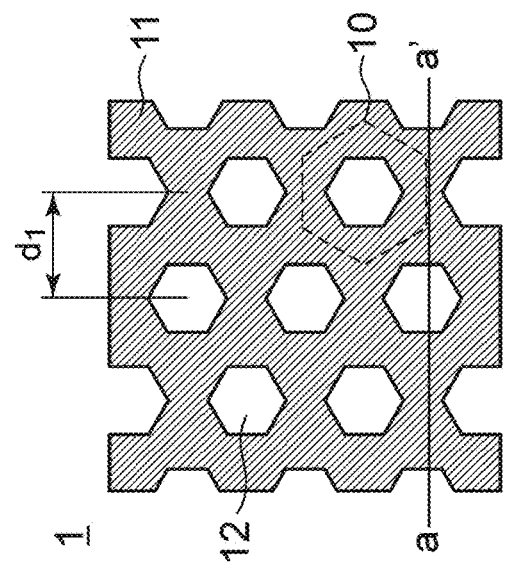
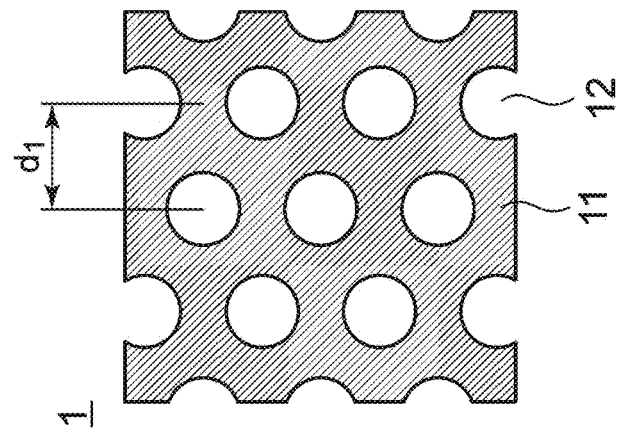
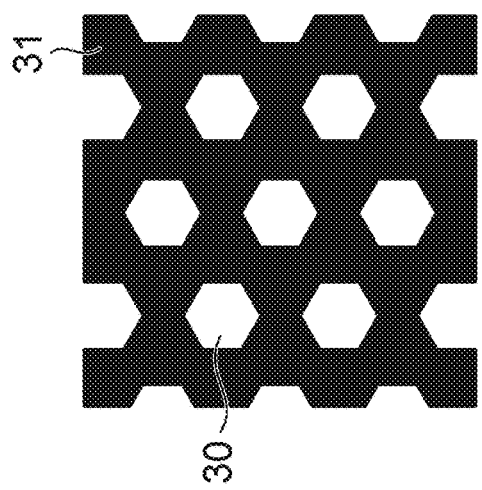

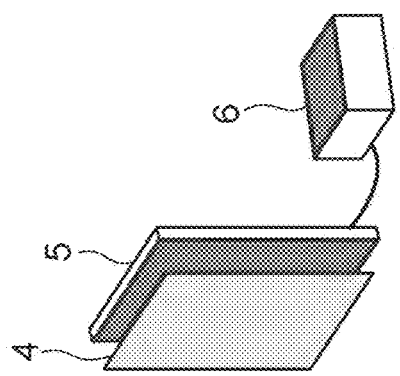
FIG. 5A
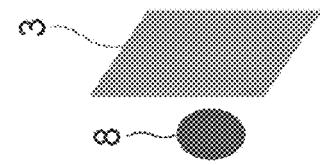
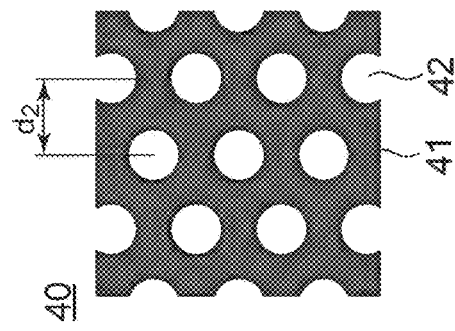
FIG. 5C
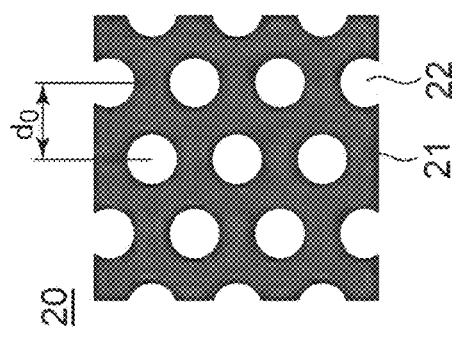
FIG. 5B

X-RAY DIFFRACTIVE GRATING AND X-RAY TALBOT INTERFEROMETER

BACKGROUND OF THE INVENTION

Field of the Invention

The present disclosure relates to an X-ray diffractive grating and an X-ray Talbot interferometer having an X-ray diffractive grating.

Description of the Related Art

An imaging method utilizing X-ray absorption by a subject has been widely used in various medical and industrial fields. Further, an imaging method utilizing a phase shift, when an X-ray passes through a subject, is developed recently. Especially, attention is made to a feature that a subject configured of a light element can be imaged with high sensitivity. Especially, a Talbot interferometer which is an imaging method utilizing an X-ray diffractive grating is widely researched.

A Talbot interferometer generally uses a plurality of "gratings" having a minute periodic structure for applying amplitude modulation or phase modulation to an incident X-ray. A "beam splitter grating", which is one of them, is a diffractive grating that diffracts an incident X-ray by a periodic structure, and forms a minute interference pattern at a predetermined position downstream of the beam by the Talbot effect. The interference pattern is called a self-image. A beam splitter grating is generally arranged near a subject in the upstream or downstream of the subject. Due to the presence of a subject, not only a change in the amplitude due to X-ray absorption by the subject but also a phase shift are caused in the transmitted X-ray. Further, scattering of the X-ray is also caused by minute fluctuations in the amplitude or phase distribution. Thereby, in the interference pattern, distortion or deterioration in visibility (also called contrast), reflecting the characteristics of the subject, occurs. By measuring changes in the interference pattern caused by the subject and performing various types of analysis, it is possible to acquire a larger amount of information than that of imaging only using absorption contrast as in the conventional case. It should be noted that as a larger amount of X-ray can be used by increasing the X-ray transmissivity of the grating, a phase modulation grating (also called phase grating) is frequently used as a beam splitter grating, rather than an amplitude modulation grating.

An interference pattern formed by a beam splitter grating is generally a minute pattern having a period of about several m. As such, in order to make it easy to perform pattern detection by an X-ray detector, an "analyzer grating", which is another grating, is often used. By matching the pitch of the analyzer grating to the period of the interference pattern, moire having a long period can be generated by superimposition of the two. As such, it is possible to acquire information of the interference pattern by a detector not having a sufficiently high spatial resolution. Further, as the phase of the moire can be shifted by moving the grating in the periodic direction, pattern analysis by the phase stepping method can be made. Further, with this configuration, even in the case where the period of the moire is very long (longer than the width of the detection range of the detector, for example), imaging of the structure of the details of the subject can be made by the spatial resolution not depending on the moire period. It should be noted that as the analyzer grating, an amplitude modulation grating (absorption grating) is often used.

Further, in order to enable an X-ray source, in which the size of an X-ray emission spot is not sufficiently small, to be used, a "source grating" may be used as a third grating. As the source grating, an amplitude modulation grating (absorption grating) is used. This grating is generally arranged near the X-ray emission spot of the X-ray source, and works to virtually divide the X-ray emission spot having a certain spatial expanse into a plurality of minute X-ray emission spots by the periodic structure. Each virtual X-ray emission spot is small in such a degree that the fringe visibility of the interference pattern generated by the action of the beam splitter grating is maintained at a certain level or more, and the virtual X-ray emission spots are arranged in a period such that interference patterns formed by adjacent virtual X-ray emission spots superimpose with each other while being shifted by the integer multiple of the period. Thereby, although a plurality of interference patterns superimpose with each other when the actual size of the X-ray emission spot is large, periodic intensity distribution of high visibility can be formed. It should be noted that a Talbot interferometer using a source grating based on such a principle is generally called a Talbot-Lau interferometer.

A grating used in an interferometer is generally a one-directional grating having a grating pattern including periodic components in only one direction. Meanwhile, a two-dimensional grating having a grating pattern including periodic components in two or more directions, like a grating pattern of a square lattice shape, may be used. A Talbot interferometer using a two-dimensional grating has an advantage that magnitude of refraction and scattering of an X-ray by a subject can be measured in a plurality of directions.

As a phase modulation pattern of a phase grating using as a beam splitter grating, various patterns can be used. U.S. Pat. No. 5,812,629 discloses some phase modulation patterns suitable for forming an interference pattern of high visibility by the Talbot effect. In most cases, a simple modulation pattern configured of two levels, namely a phase advance portion and a phase delay portion, is used in practice, due to easiness in fabrication of the grating. For example, a one-dimensional grating having a structure in which phase advance portions and phase delay portions of the equal width are alternately arrayed and giving phase modulation of a height of $\pi/2$ to an X-ray of assumed photon energy is one of phase gratings which are often used, generally.

Further, "X-ray Talbot Interferometry with Capillary Plates" by A. Momose and S. Kawamoto, Japanese Journal of Applied Physics, Vol. 45, No. 1A, 314-316 (2006), describes a Talbot interferometer in which capillary plates are used for a beam splitter grating and an analyzer grating, as two-dimensional absorption gratings.

In a Talbot interferometer, the amounts relating to phase shift and scattering by a subject are measured according to changes in the interference pattern formed by the Talbot effect. As such, increasing the visibility of the detected interference pattern is an important element for performing highly reliable measurement.

Meanwhile, the Talbot effect is an effect based on a diffraction phenomenon of a wave, and the diffraction phenomenon is generally a phenomenon depending on the wavelength. Further, the phase modulation amount itself, by the phase grating, also changes according to the wavelength of the X-ray. Accordingly, the visibility of an interference pattern at a particular position downstream of the phase grating generally changes complicatedly by the wavelength of the X-ray to be used.

Further, wavelength dependency of the visibility of such an interference pattern is unique to the structure of a diffractive grating. In the present description, such wavelength dependency (may also be considered as photon energy dependency) of the visibility of an interference pattern may be called achromaticity of a diffractive grating. It should be noted that achromaticity is high indicates that wavelength dependency of the visibility of an interference pattern is low.

An X-ray available by an X-ray source such as an X-ray tube, which is generally used, has relatively wide energy spectrum. As such, one in which achromaticity of the phase grating is high can form an interference pattern of high visibility at a particular position, by using a wide range of energy components of the irradiated X-ray, and such components can be used for measurement.

SUMMARY OF THE INVENTION

It is therefore an aspect of the disclosure to provide an X-ray diffractive grating in which visibility of an interference pattern formed at a particular position by the Talbot effect is higher with respect to an X-ray having a wider range of energy than a conventional one.

An aspect of an X-ray diffractive grating of the disclosure is an X-ray diffractive grating including a phase advance portion and a plurality of phase delay portions. The phase advance portion includes a grating material. In each of the phase delay portions, the thickness of the grating material is less than that in the phase advance portion, and the area occupancy of the phase delay portions in the corresponding two-dimensional grating pattern is 15% or more but less than 45%. The phase delay portions are arranged in a hexagonal lattice shape. Other aspects of the disclosure will be described in the description of the embodiments.

Further features and aspects of the disclosure will become apparent from the following description of example embodiments (with reference to the attached drawings).

BRIEF DESCRIPTION OF THE DRAWINGS

FIGS. 1A to 1C illustrate examples of grating patterns of a diffractive grating according to an embodiment and an example of an interference pattern formed by a diffractive grating.

FIGS. 5A to 5C illustrate a schematic diagram of a Talbot interferometer including the diffractive grating according to the example embodiment.

DESCRIPTION OF THE EMBODIMENTS

Figure 2B:
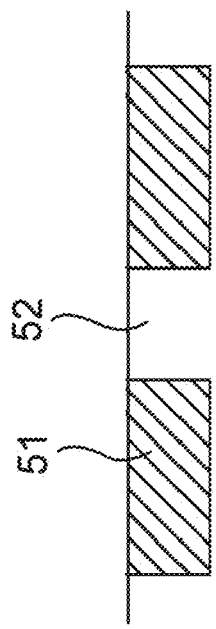
FIGS. 2A and 2B illustrate example sectional views of the diffractive grating according to the example embodiment.

Hereinafter, various aspects and example embodiments of the disclosure will be described in detail based on the accompanying drawings.

It should be noted that in the respective drawings, the same member is denoted by the same reference numeral and the description is not repeated herein.

As a result of earnest consideration by the inventor of the disclosure, it is found that when the following three conditions are satisfied in an X-ray diffractive grating having a hexagonal grating pattern, the X-ray diffractive grating is able to form an interference pattern of high visibility and exhibits high achromaticity.

(1) It is a phase grating having a structure that in a corresponding two-dimensional grating pattern, a plurality of phase delay portions are arranged in a hexagonal lattice shape in the phase advance portion.

(2) The phase delay portion is configured such that the thickness of a grating material is thinner than that of the phase advance portion (in other words, the phase delay portion is dented).

(3) Area occupancy of the phase delay portion in the corresponding two-dimensional grating pattern is 15% or more but less than 45%.

FIG. 1A illustrates an example of a two-dimensional grating pattern of an X-ray diffractive grating satisfying the three conditions described above. A grating pattern 1 includes a phase advance portion 11 and a plurality of phase delay portions 12. The phase delay portions 12 are arranged in a hexagonal lattice shape in the phase advance portion 11. The shape of each phase delay portion 12 is a regular hexagon, and the area occupancy of the phase delay portion 12 (hereinafter may be simply referred to as area occupancy) is one third. It should be noted that area occupancy of the phase delay portion means the rate of the area of the phase delay portion 12 relative to the area of the basic structure 10 of the two-dimensional grating pattern of the X-ray diffractive grating. It should be noted that the basic structure 10 may be a structure having a regular hexagonal external shape forming a minimum unit of a hexagonal grating pattern including one phase delay portion 12 and the phase advance portion 11 surrounding it. Accordingly, the phase grating pattern in a hexagonal lattice shape in the present embodiment is a grating pattern in which the basic structures 10, each having a regular hexagonal external shape, are laid in a plane. It should be noted that the center of the phase delay portion 12 and the center of the basic structure 10 agree with each other. At this time, a distance between a side forming a part of the contour of the basic structure 10 and the center of the phase delay portion 12 corresponds to a half of the distance between the centers of the adjacent phase delay portions 12. It should be noted that the center of a phase delay portion means a geometrical center of gravity of the shape of each phase delay portion. Similarly, the center of the basic structure 10 indicates a geometrical center of gravity of the regular hexagon showing the external shape of each basic structure 10. It should be noted that the shape of the phase delay portion indicates a sectional shape of the phase delay portion in a plane vertical to the incident direction of an X-ray, in principle.

Further, FIG. 1B illustrates an example grating pattern in the case where the shape of a phase delay portion 12 is a circle. This grating pattern 1 is a grating pattern 1 approximate to the grating pattern 1 of FIG. 1A as a whole. The area occupancy of this grating pattern 1 is also one third.

It should be noted that an actual grating may be fabricated including some manufacturing errors. For example, when a grating pattern is a pattern elongated in one direction as a whole, the external shape of the basic structure may be in a shape slightly deformed from a regular hexagon.

A phase grating having the pattern illustrated in FIG. 1A forms an interference pattern of a hexagonal lattice shape in which a plurality of bright portions 30 are arranged in a uniform dark portion 31 as illustrated in FIG. 1C, by diffracting an X-ray. An interference pattern in a hexagonal lattice shape indicates an interference pattern in which basic interference patterns, each having a regular hexagonal external shape, are laid without any space in a plane. Even in the case where each of the phase delay portions is in a circular shape as illustrated in FIG. 1B, an interference pattern similar to the interference pattern illustrated in FIG. 1C is formed.

A grating pitch $d_1$ in the grating pattern of the hexagonal lattice shape is a distance illustrated in FIGS. 1A and 1B. The distance corresponds to a height of a smallest regular triangle formed by linking the centers of three phase delay portions 12.

Figure 2A:
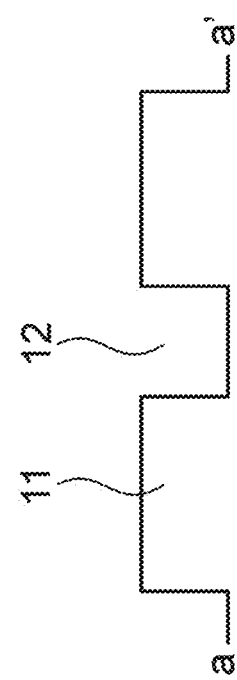

Even in the case of adopting either example pattern of FIG. 1A or 1B, as the thickness of the grating material in the phase delay portion 12 is thinner than that in the surrounding phase advance portion 11, a relative phase delay is generated in the transmitted X-ray. It should be noted that the thickness of the grating material means the thickness in the incident direction of the X-ray. FIG. 2A illustrates a cross-sectional view of a diffractive grating according to the present embodiment having the grating pattern illustrated in FIG. 1A. FIG. 2A is a sectional view taken along a-a' in FIG. 1A. As illustrated in FIG. 2A, the structure of the diffractive grating according to the present embodiment is a structure in which a plurality of holes for forming phase delay portions is arrayed on the grating substrate. These holes may be holes not penetrating (dents) as illustrated in FIG. 2A, or through holes. It is preferable that these holes are holes shaped like well having high verticality. In the case where the phase delay portion is a through hole, the phase delay portion does not have a grating material. Even in that case, however, in the disclosure and the present description, it is described that the thickness of the grating material in the phase delay portion is thinner than that in the phase advance portion.

In the disclosure and the present description, a grating structure in which such holes are arrayed may be called a hole-array type structure. On the contrary, a grating structure in which a plurality of columnar structures is arrayed on the grating substrate may be called a pillar-array type structure in the disclosure and the present description.

Figure 3:
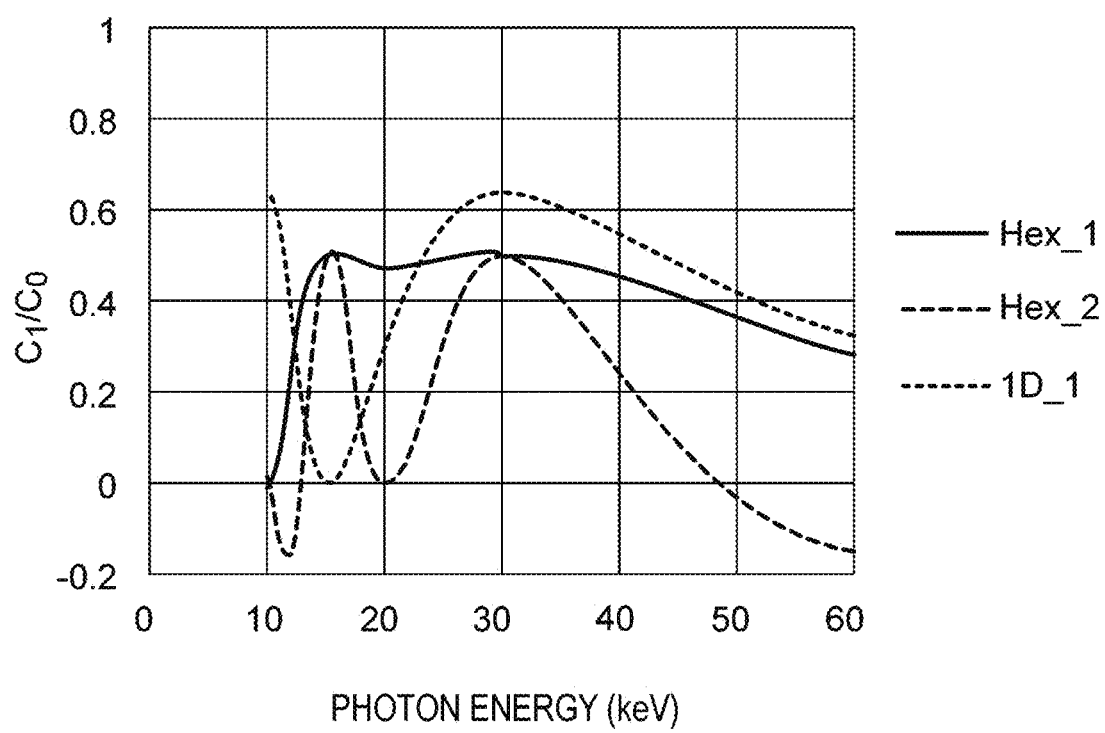
FIG. 3 illustrates X-ray energy dependency of visibility of interference patterns formed by the diffractive grating according to the example embodiment and comparative examples.

FIG. 3 illustrates results of calculating dependency of the visibility of interference patterns on the X-ray photon energy (hereinafter may be referred to as visibility energy dependency) of the diffractive gratings according to the present embodiment and comparative examples. Here, $c_1/c_0$ shown on the axis of ordinates of the graph is a ratio of a base wave component ($c_1$) to a DC component ($c_0$) when the X-ray intensity distribution of the interference pattern is developed into a complex Fourier series, and is used as an index of visibility of the interference pattern in this example. While $c_1$ is a complex number generally, it is calculated only for the case where it takes a real value in this example. Further, as the bright portion and the dark portion of the interference pattern are inversed between the time when the value of $c_1/c_0$ is positive and the time when it is negative, when these patterns exist at the same time, they have a relationship of weakening the visibility. As such, it is not preferable generally. Further, in an X-ray region, δ which is a decrement from unity of the refractive index of a substance is almost in proportion to the square of a wavelength A of the X-ray, generally. As such, in the present description, each calculation is performed based on an assumption that $δ∝λ^2$. Further, calculation is performed based on an assumption that there is no X-ray absorption by the grating material. It should be noted that the designs of the three grating structures, illustrated in FIG. 3, are optimized to the X-ray photon energy of 30 keV. As 30 keV in this case, energy of the X-ray assumed when designing the grating may be called an assumed energy value in the present description.

A curve line (solid line) illustrated as Hex_1 in FIG. 3 is a result of calculating visibility ($c_1/c_0$) of an interference pattern when the grating pattern of FIG. 1A is adopted. In this calculation, the thickness of the grating material of a region corresponding to the phase delay portion 12 is made thinner than that of the phase advance portion 11 such that the phase delay amount becomes $2π/3$ with respect to the X-ray having the photon energy of 30 keV. It should be noted that in the present description and the disclosure, the phase delay amount indicates a relative phase delay amount of the X-ray passing thorough the phase delay portion 12, with respect to the X-ray passing through the phase advance portion 11.

Further, the position where the visibility of the interference pattern is evaluated is set to be a position $(2/3)·d_1^2/λ_{30keV}$ downstream of the grating, where $λ_{30keV}$ is a wavelength corresponding to the X-ray of 30 keV. This position is a position where an interference pattern formed by the diffractive grating having the structure described above appears with high visibility. As understood from FIG. 3, in this grating structure, energy dependency of the visibility is low, and high visibility can be maintained from near 15 keV to 40 keV or more.

Figure 6A:
FIGS. 6A and 6B illustrate grating patterns of diffractive gratings according to comparative examples.

Meanwhile, a curve line (dotted line) illustrated as 1D_1 in FIG. 3 is a result of calculating visibility ($c_1/c_0$) of an interference pattern when adopting a grating pattern in which phase advance portions 111 and phase delay portion 112, having the same width as illustrated in FIG. 6A, are alternately arrayed. In this calculation, the phase delay amount of the X-ray is set to be $π/2$ with respect to the X-ray having the photon energy of 30 keV. This grating structure has been often used conventionally. Further, the position where the visibility of the interference pattern is evaluated is a position $(1/2)·d_{1(1D)}^2/λ_{30keV}$ downstream of the grating. This position is a position where an interference pattern formed by the diffractive grating having the structure described above appears with high visibility. It should be noted that $d_{1(1D)}$ represents a grating pitch of a one-dimensional grating.

As understood from FIG. 3, in this grating structure, energy dependency of the visibility is higher (achromaticity is relatively low) compared with that of Hex_1, such that the visibility drops to zero near 15 keV. It should be noted that while an absolute value of the visibility near 30 keV is higher than that of Hex_1, in the interference pattern of a hexagonal lattice shape, as there are periodic components relating to three directions and all of them can be used for measuring the subject information, a difference in the absolute value of the visibility can be supplemented to a certain extent.

Figure 6B:
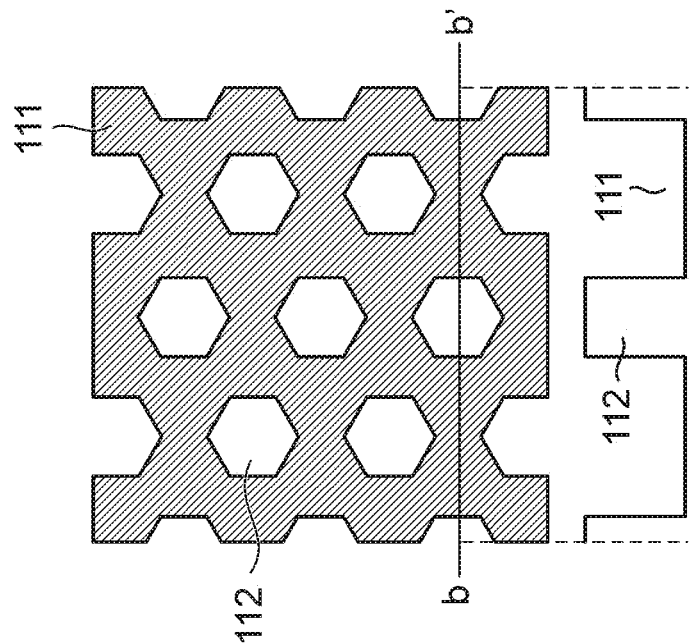

Meanwhile, a curve line (broken line) illustrated as Hex_2 in FIG. 3 is a result of calculating the visibility ($c_1/c_0$) of an interference pattern in the case where the grating structure is not a hole-array type but a pillar-array type, although a grating pattern similar to that of FIG. 1A is adopted. FIG. 6B illustrates a grating pattern and a sectional view of this grating. The grating pattern configured of the phase advance portion 111 and the phase delay portions 112 is the same as the grating pattern of Hex_1 illustrated in FIG. 1A. In the X-ray passing through the columnar structural portion (phase delay portion 112) on the grating substrate, as the phase advances more compared with the surrounding, it serves as a phase advance portion actually. However, as a case where the phase advance amount is $4π/3$ with respect to the X-ray of 30 keV is assumed, this equals to giving a phase delay of $2\pi/3$ to the X-ray of 30 keV. As such, although the phase delay portion 112 is a phase advance portion actually, it can be said that the phase delay portion 112 having a phase delay amount of $2\pi/3$ is simulatively formed. As such, the grating structures of Hex_1 and Hex_2 can be considered to be the same grating with respect to the X-ray of 30 keV. Further, the position where the visibility of the interference pattern is evaluated is a position that is $(2/3) \cdot d_1^2/\lambda_{30keV}$ downstream of the grating, which is the same as Hex_1. As understood from FIG. 3, in this grating structure, energy dependency of the visibility is higher than that of Hex_1 (achromaticity is relatively low) such that the visibility drops to zero near 20 keV, for example. As described above, although the grating structure can be considered as the same grating as that of Hex_1 with respect to the X-ray of 30 keV, there is a large difference when the energy dependency of the visibility is compared as a whole. As such, it is understood that the achromaticity is lower compared with that of Hex_1.

From the comparison described above, it is understood that the hole-array type phase grating having the grating pattern of FIG. 1A has higher achromaticity than that of a phase grating having another grating structure. Meanwhile, even in the case of the identical phase grating, when the energy of the X-ray to be used changes, the phase delay amount also changes. For example, the grating of Hex_1 in FIG. 3 is a phase grating which has a phase delay amount of $2\pi/3$ with respect to the X-ray of 30 keV, but has a phase delay amount of almost $\pi$ with respect to the X-ray of 20 keV. As such, in order to estimate the phase delay amount on the design, it is necessary to know an assumed energy value of the X-ray. Further, regarding the phase delay portion of the phase grating of the present embodiment, it is preferable that the phase delay amount of the X-ray in an assumed energy value is within a range of $2\pi/3 \pm \pi/6$ ($3\pi/6$ or more but $5\pi/6$ or less).

When an assumed energy value of the X-ray is unknown, an average value of the photon energy of the X-ray to be irradiated to the phase grating may be regarded as an assumed energy value, for example. In another case, it is also possible to obtain an assumed energy value based on a distance L between a face on which detection of an interference pattern is performed and the phase grating in the optical system. On the assumption that an X-ray wavelength corresponding to an assumed energy value is $\lambda_A$, a condition on which an interference pattern having high visibility can be obtained is $L=(2/3) \cdot d_1^2/\lambda_A$, as described above. Accordingly, $\lambda_A$ and a corresponding assumed energy value can be calculated from $\lambda_A=(2/3) \cdot d_1^2/L$, provided that this calculation formula assumes an incident X-ray in a plane wave form. In general, an X-ray made incident on a phase grating is in a spherical wave form centering around the X-ray source or a virtual X-ray source formed by a source grating in a Talbot-Lau interferometer, and the position where the interference pattern is obtained is shifted downstream than the case where a plane wave is assumed. In order to consider this effect, it is only necessary to calculate $\lambda_A$ according to $\lambda_A=(2/3) \cdot d_1^2 \cdot (1+L_{12}/L_{01})/L_{12}$, where $L_{01}$ represents a distance from the X-ray source or the virtual X-ray source to the phase grating, and $L_{12}$ represents a distance from the phase grating to the position where the interference pattern is detected. In the case where the optical system constitutes a Talbot interferometer using the phase grating of the present embodiment as a beam splitter grating, the distance $L_{12}$ indicates a distance between the beam splitter grating and the analyzer grating. In the case where the optical system is a Talbot interferometer not having an analyzer grating, the distance $L_{12}$ indicates a distance between the beam splitter grating and the detector.

Next, a relationship between the area occupancy of the phase delay portion and the achromaticity of the grating in the basic structure will be described.

Figure 4B:
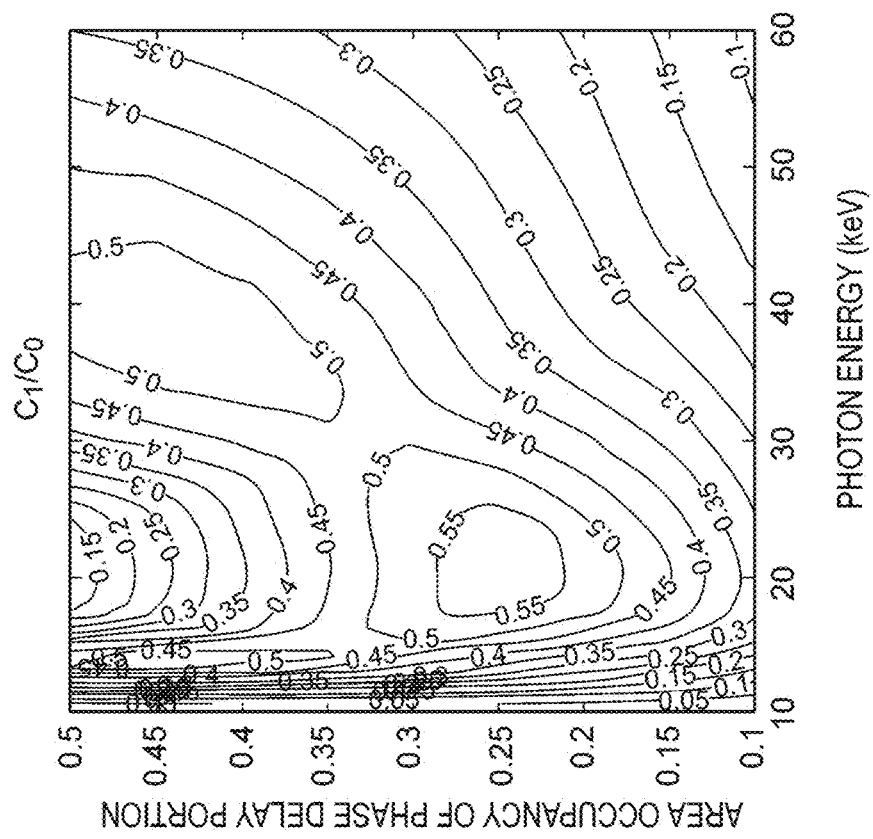
FIGS. 4A and 4B each illustrate a relationship between area occupancy of a phase delay portion in a grating pattern of the diffractive grating and achromaticity according to the example embodiment.
Figure 4A:
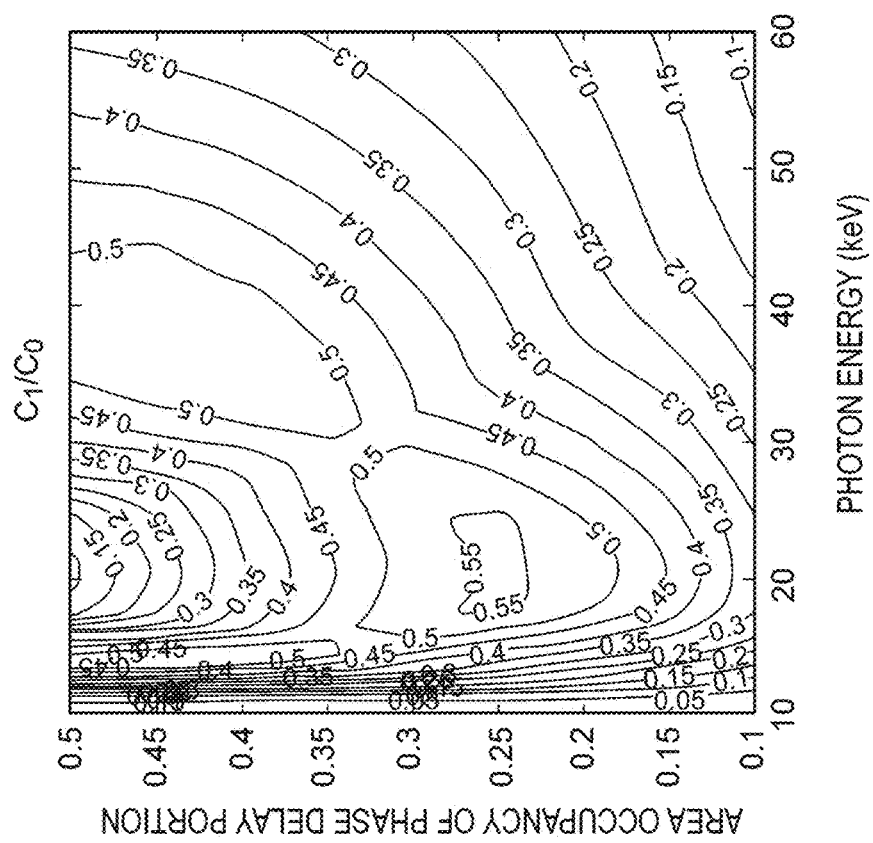

FIG. 4A illustrates a relationship between the area occupancy of the phase delay portion 12 in the basic structure and the achromaticity, regarding the grating pattern having the phase delay portion 12 of a regular hexagonal shape as illustrated in FIG. 1A. In FIGS. 4A to 4B, values of $c_1/c_0$ on the respective conditions are shown by a contour line map. The conditions other than the area occupancy of the phase delay portion 12 are the same as the calculation conditions of the curve line of Hex_1 in FIG. 3. This means that the grating structure is a hole-array type, and a difference in the thickness of the grating material between the phase advance portion 11 and the phase delay portion 12 (corresponding to the depth of the hole for forming the phase delay portion 12) is a value in which the phase delay amount becomes $2\pi/3$ with respect to the X-ray of 30 keV. Further, the position where the visibility of the interference pattern is evaluated is a position downstream by $(2/3) \cdot d_1^2/\lambda_{30keV}$ of the grating. As understood from FIGS. 4A to 4B, when the area occupancy is about 15% or more but less than 45%, relatively large visibility is obtained with respect to a wide range of X-ray energy. At this time, with respect to three types of X-ray energy of 20 keV, 30 keV, and 40 keV, a $c_1/c_0$ value is maintained at 0.2 or more. Further, when the area occupancy is about 30% or more but less than 35%, uniformly higher visibility is obtained with respect to a wide range of X-ray energy. At this time, with respect to three types of X-ray energy of 20 keV, 30 keV, and 40 keV, a $c_1/c_0$ value is maintained at 0.4 or more.

Further, FIG. 4B illustrates a calculation result in the case where the phase delay portion 12 has a grating pattern of a circular shape, as illustrated in FIG. 1B. The conditions other than the shape of the phase delay portion are the same as those of FIG. 4A. There is no large difference between the calculation results of FIGS. 4A and 4B. As such, it is understood that the shape of the phase delay portion 12 is not highly important, regarding the achromaticity of the grating. As such, the shape of the phase delay portion 12 does not matter particularly. Further, a grating pattern in which the phase delay portion 12 of a regular hexagonal shape in FIG. 1A is turned at a certain angle without moving the center position thereof is also acceptable, on the same grounds. However, in the case where the shape of the phase delay portion 12 is significantly different from a regular hexagon or a circle, the interference pattern and the visibility thereof on the respective conditions may be changed significantly. Accordingly, it is preferable that the shape of the phase delay portion 12 is close to a regular hexagon or a circle. It is also preferable that the largest value of a distance between the center of the phase delay portion and the contour of the phase delay portion is 1.2 times or less of the smallest value. It should be noted that when the largest value of the distance between the center of the phase delay portion and the contour of the phase delay portion equals to the smallest value, the phase delay portion is a perfect circle.

In the present embodiment, description has been given on the case where the grating is configured of a single grating material and phase modulation is caused by a thickness difference. However, it is also acceptable to use another grating structure in which the thickness is uniform but the phase advance portion 11 and the phase delay portion 12 are formed of materials which are different in the refractive index to thereby cause phase modulation. FIG. 2B is a sectional view of a diffractive grating having such a structure. A material 51 having a large δ value is considered as a grating material, and a difference in the δ value with a material 52 having a small δ value is considered as an effective δ value, whereby the argument given above is applicable as it is. It should be noted that as δ represents a decrement of the refractive index from 1, the refractive index of the material 52 having a smaller δ value is closer to 1 compared with the refractive index of the material 51 having a larger δ value. In FIG. 2B, the diffractive grating is configured of the material 52 of a smaller δ value and the material 51 of a larger δ value. The diffractive grating can be produced by forming arrays of a columnar structure on the substrate made of the material 52 of a smaller δ value, and filling the gap portions with the material 51 of a larger δ value. It should be noted that a material having a larger δ value is usually a material having a large mass density.

A Talbot interferometer having a diffractive grating of the present embodiment will be described. FIG. 5A is a schematic diagram of a Talbot interferometer. The Talbot interferometer 100 is a Talbot-Lau interferometer having a source grating 2. An X-ray Talbot interferometer 100 includes an X-ray source 7, the source grating 2, a beam splitter grating 3, an analyzer grating 4, an X-ray detector 5, and an arithmetic operation device 6.

The X-ray source 7 irradiates X-ray to the source grating 2. It should be noted that the Talbot interferometer 100 may not include the X-ray source 7. Even in that case, the X-ray source 7 and the Talbot interferometer 100 are used in combination with each other at the time of imaging. As the X-ray source 7 and the Talbot interferometer 100 are separated, the X-ray source 7 can be replaced according to the service life of the X-ray source 7 or according to the energy of the X-ray used for imaging. The Talbot interferometer may not include the X-ray source 7, and imaging may be performed by combining it with an X-ray source in which the energy, output, focal spot size, and the like match the radiographing conditions. In that case, the Talbot interferometer may include a unit for positioning an X-ray source (a mount on which an X-ray source is disposed, for example).

FIG. 5B illustrates an example of a grating pattern 20 of a source grating. The source grating 2 includes X-ray shielding portions 21 and transmitting portions 22, and when the X-ray is irradiated from the X-ray source 7, virtually forms an array of minute X-ray sources. As illustrated in FIG. 5B, the transmitting portions 22 are arranged in a hexagonal lattice shape.

The beam splitter grating 3 diffracts the X-ray from the source grating 2 to form an interference pattern. As the beam splitter grating 3, the diffractive grating described above can be used.

FIG. 5C illustrates an example of a grating pattern 40 of the analyzer grating. The analyzer grating 4 includes X-ray shielding portions 41 and transmitting portions 42, and forms moire by shielding a part of the bright portion of the interference pattern. The pitch of the moire can be determined appropriately. For example, when the pitch $d_2$ of the analyzer grating 4 and the pitch of the interference pattern are allowed to match each other and the periodic direction is also allowed to match, the pitch of the moire is infinity. In the disclosure and the present description, even if the pitch is infinity, the intensity distribution formed by the X-ray passing through the analyzer grating 4 is called moire. It should be noted that it is only necessary that both the shielding portion 21 of the source grating and the shielding portion 41 of the analyzer grating shield about eighty percent of the X-ray made incident in parallel with the thickness direction.

The X-ray detector 5 is an area sensor in which pixels that detect the X-ray passing through the analyzer grating 4 are arrayed in two directions. Although it is possible to use a line sensor instead of the area sensor and perform scanning by the sensor to acquire two-dimensional intensity distribution, it is preferable to use an area sensor because the time taken for imaging can be reduced.

The arithmetic operation device 6 acquires information of a subject with use of the detection result by the X-ray detector 5. In general, information of a subject is acquired by applying fringe analysis to the detection result. In the case of using the detection result directly as an image of the subject, the arithmetic operation device 6 acquires the detection result from the X-ray detector 5, converts the information as required, and transmits it to an image display unit. It should be noted that the arithmetic operation device 6 may not be independent from the X-ray detector 5. An X-ray detector, having a function of converting the detection result into information that can be received by the image display unit, may be used as the arithmetic operation device 6 integrated with the X-ray detector 5. Further, the Talbot interferometer may be in a form not including the arithmetic operation device 6. For example, it is possible to connect a general-purpose computer with the X-ray detector 5 at the time of measurement, and use the general-purpose computer as the arithmetic operation device 6, for example.

It should be noted that while the Talbot interferometer 100 illustrated in FIG. 6A includes the source grating 2, if the X-ray source 7 is sufficiently small and visibility of the interference pattern formed by the beam splitter grating 3 can be obtained sufficiently without using a source grating, the source grating 2 is unnecessary. Further, if the X-ray detector 5 has spatial resolution of a level capable of detecting the interference pattern formed by the beam splitter grating 3, the analyzer grating 4 may be unnecessary.

When the Talbot interferometer 100 includes a diffractive grating having high achromaticity, as the visibility of the interference pattern can be increased with respect to a wide range of X-ray energy, a wide range of energy components can be used for measurement.

EXAMPLE 1

Example 1 is a specific example of a diffractive grating according to the embodiment. An X-ray diffractive grating of Example 1 has a grating pattern which is the same as that illustrated in FIG. 1A, and the area occupancy of the regular hexagonal phase delay portion 12 in the basic structure is one third. The grating structure is of hole-array type, and the grating material is silicon. The depth of a hole for forming the phase delay portion 12 is 26 μm, thereby the phase delay amount with respect to the transmitted X-ray having the photon energy of 30 keV is about $2\pi/3$. Further, the grating pitch $d_1$ is 4 μm. It should be noted that the wave length of the X-ray having the energy of 30 keV is about 0.041 nm. As such, a distance L to a position where the diffractive grating forms an interference pattern of high visibility is calculated as $L=(2/3)\cdot(4\ \mu m)^2/0.041\ nm \approx 260$ mm. This interference pattern has high visibility with respect to the X-ray energy of a wide range from near 15 keV to 40 keV or larger. It should be noted that the distance L is a value on the assumption that incident X-ray is a plane wave. As such, in practice, it is desirable to use it while considering a change in the optimum distance such that the distance becomes optimum with respect to the spherical wave generated from the X-ray source or the virtual X-ray source formed by the source grating in the Talbot-Lau interferometer. Specifically, a distance $L_{12}$, from the diffractive grating to a position where the interference pattern is detected, is desirably calculated from $L_{12}=L_{01}L/(L_{01}-L)$, where $L_{01}$ represents a distance from the X-ray source or the virtual X-ray source to the phase grating.

While a preferable embodiment of the disclosure has been described above, the disclosure is not limited to the embodiment. Various deformations and changes can be made within the scope thereof.

While the disclosure has been described with reference to example embodiments, it is to be understood that the invention is not limited to the disclosed example embodiments. The scope of the following claims is to be accorded the broadest interpretation so as to encompass all such modifications and equivalent structures and functions.

This application claims the benefit of Japanese Patent Application No. 2015-215212, filed Oct. 30, 2015, which is hereby incorporated by reference herein in its entirety.

What is claimed is:

1. An X-ray Talbot interferometer comprising:
   an X-ray diffractive grating including a phase advance portion including a grating material and a plurality of phase delay portions arranged in a two-dimensional grating pattern; and
   an X-ray detector,
   wherein a thickness of the phase delay portions is less than that of the phase advance portion,
   wherein an area occupancy of the phase delay portions hexagonally arranged in a hole-array manner in the X-ray diffractive grating is 15% or more but less than 45%, and
   wherein a visibility value of an interference pattern in downstream of the X-ray diffractive grating is 0.2 or more at a range between 20 keV and 40 keV in an X-ray energy.

2. The X-ray Talbot interferometer according to claim 1, wherein the area occupancy of the phase delay portions in the two-dimensional grating pattern is 30% or more but less than 35%.

3. The X-ray Talbot interferometer according to claim 1, wherein the visibility value of an interference pattern in downstream of the X-ray diffractive grating is 0.4 or more at a range between 20 keV and 40 keV in an X-ray energy.

4. The X-ray Talbot interferometer according to claim 1, wherein the X-ray diffractive grating has a grating structure in which a phase delay amount of an X-ray passing through the phase delay portion with respect to an X-ray passing through the phase advance portion is within a range of $2\pi/3\pm\pi/6$.

5. The X-ray Talbot interferometer according to claim 1, wherein the X-ray diffractive grating has a grating structure in which a phase delay amount of an X-ray passing through the phase delay portion with respect to an X-ray passing through the phase advance portion is $2\pi/3$.

6. The X-ray Talbot interferometer according to claim 1, wherein the plurality of phase delay portions are shaped in circular or hexagonally.

7. The X-ray Talbot interferometer according to claim 1, wherein the thickness of the grating material in each of the phase delay portions is 0.

8. The X-ray Talbot interferometer according to claim 1, wherein the phase delay portion has another material different from the grating material in a refractive index to an X-ray.

9. The X-ray Talbot interferometer according to claim 8, wherein the refractive index to the X-ray of the other material is closer to 1, compared with the refractive index of the grating material.

* * * * *